United States Patent
Leeton et al.

(10) Patent No.: US 10,722,861 B2
(45) Date of Patent: Jul. 28, 2020

(54) REACTOR SYSTEM FOR USE WITH AN IONIC LIQUID CATALYST

(71) Applicant: UOP LLC, Des Plaines, IL (US)

(72) Inventors: Eric Leeton, Corpus Christi, TX (US); Kurt Detrick, Glen Ellyn, IL (US); Christian D. Freet, Chattaroy, WA (US); David S. Lafyatis, Schaumburg, IL (US); Robert Mehlberg, Wheaton, IL (US); Sean G. Mueller, Des Plaines, IL (US); Gregory J. Schrad, Naperville, IL (US); Zhanping Xu, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/987,859

(22) Filed: May 23, 2018

(65) Prior Publication Data

US 2018/0264431 A1 Sep. 20, 2018

Related U.S. Application Data

(63) Continuation of application No. PCT/US2016/065696, filed on Dec. 9, 2016.

(60) Provisional application No. 62/265,649, filed on Dec. 10, 2015.

(51) Int. Cl.
*B01J 19/24* (2006.01)
*C07C 2/58* (2006.01)

(52) U.S. Cl.
CPC ......... *B01J 19/2415* (2013.01); *B01J 19/242* (2013.01); *C07C 2/58* (2013.01); *B01J 2219/00078* (2013.01); *B01J 2219/00081* (2013.01); *B01J 2219/00083* (2013.01); *B01J 2219/24* (2013.01)

(58) Field of Classification Search
CPC .............. B01J 19/2415; B01J 19/242; B01J 2219/00083; B01J 2219/00078; B01J 2219/24; B01J 2219/00081; C07C 2/58
See application file for complete search history.

(56) References Cited

U.S. PATENT DOCUMENTS

| | | | |
|---|---|---|---|
| 4,161,497 A | 7/1979 | Makovec et al. |
| 4,780,217 A | 10/1988 | Petersen |
| 5,284,990 A | 2/1994 | Petersen et al. |
| 5,785,933 A | 7/1998 | Cunningham et al. |

(Continued)

FOREIGN PATENT DOCUMENTS

| | | |
|---|---|---|
| CN | 1313422 A | 9/2001 |
| JP | 2004161763 A | 6/2004 |

(Continued)

OTHER PUBLICATIONS

Chemical Process Equipment, Selection and Design (2010, Chapter 8: Heat Transfer and Heat Exchanger, p. 196). (Year: 2010).*

(Continued)

*Primary Examiner* — Ali Z Fadhel

(57) ABSTRACT

Reactor systems for use with ionic liquid catalyst. The reactor systems include one or more stages, which include a reactor and a heat exchanger, and a separation zone. The reactor and the heat exchanger may have a vertical orientation. Additionally, a separation vessel may also include a vertical orientation. The heat exchanger may allow for linear flow of process fluid to control residence time.

20 Claims, 3 Drawing Sheets

(56) References Cited

U.S. PATENT DOCUMENTS

| | | | |
|---|---|---|---|
| 6,106,789 A | 8/2000 | Thompson et al. | |
| 6,943,276 B1 | 9/2005 | Mehlberg et al. | |
| 7,377,307 B1 | 5/2008 | Ijiri et al. | |
| 7,947,232 B2 | 5/2011 | Strauss et al. | |
| 8,414,840 B2 | 4/2013 | Filippi et al. | |
| 8,921,636 B2 | 12/2014 | Cleverdon et al. | |
| 2013/0066130 A1 | 3/2013 | Luo et al. | |
| 2016/0002125 A1* | 1/2016 | Luo | C07C 2/62 585/447 |
| 2016/0264494 A1* | 9/2016 | Mohr | C07C 2/58 |

FOREIGN PATENT DOCUMENTS

| | | |
|---|---|---|
| WO | 2006065427 A2 | 6/2006 |
| WO | 2009002967 A2 | 12/2008 |
| WO | 2009101434 A2 | 8/2009 |
| WO | 2011015662 A2 | 2/2011 |
| WO | 2014004232 A1 | 1/2014 |
| WO | 2014201767 A1 | 12/2014 |

OTHER PUBLICATIONS

International Search Report from corresponding PCT Application No. PCT/US2016/065696, dated Mar. 16, 2017.
Written Opinion from corresponding PCT Application No. PCT/US2016/065696, completed Feb. 27, 2017.
International Preliminary Report on Patentability from corresponding PCT Application No. PCT/US2016/065696, dated Jun. 12, 2018.
Qiao, Cong-zhen et al., Recycling and Activity Recovery of Chloroaluminate Ionic Liquid as Catalyst for Alkylation of Benzene with 1-Dodecene, The Chinese Journal of Process Engineering, vol. 6, No. 2, Apr. 2006.

* cited by examiner

REACTOR SYSTEM FOR USE WITH AN IONIC LIQUID CATALYST

CROSS-REFERENCE TO RELATED APPLICATIONS

This application is a Continuation of copending International Application No. PCT/US2016/065696 filed Dec. 9, 2016, which application claims priority from U.S. Provisional Application No. 62/265,649 filed Dec. 10, 2015, the contents of which cited applications are hereby incorporated by reference in their entirety.

RELATED APPLICATIONS

The invention relates to a reactor system for use with ionic liquid catalyst, preferably in an alkylation process, and more particularly, the invention relates to reactor system having vertically orientated vessels.

FIELD OF THE INVENTION

Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, as well as temperatures, the ionic liquid can have very different properties.

Ionic liquids have been used to catalyze a variety of hydrocarbon conversion processes, such as alkylation, isomerization, disproportionation, and the like. When ionic liquids are used to catalyze hydrocarbon conversion processes, the ionic liquid catalyst is typically dispersed into droplets to provide intimate contact between the reactants and the ionic liquid catalyst. The mixture of ionic liquid, reactants, and reaction products are typically separated by gravity into two phases, a heavier ionic liquid phase and a lighter hydrocarbon phase.

Typically, the reactors, heat exchangers and separation vessels used in an ionic liquid reactor system require a relatively large amount of plot space given the required time and volume necessary for facilitating the reaction, for separating the effluent into the two phases, and for heat removal. The plot space may be a critical issue in various locations as the revamping of existing HF or sulfuric acid catalysts units may lack the requisite space for additional vessels and equipment to be used with the ionic liquid catalyst.

Therefore, there is a continuing need for reactor systems that efficiently and efficiently utilize ionic liquid catalyst without requiring as much plot space.

Accordingly, the present invention is directed at providing a separation vessel that addresses one or more of these drawbacks associated with the conventional separation vessels used for separating an effluent having ionic liquid.

SUMMARY OF THE INVENTION

One or more new reactor systems have been invented which efficiently and effectively utilize ionic liquid catalyst. The plot space for accommodating the ionic liquid alkylation equipment is reduced by using some reactors, heat exchangers, and/or separators that are oriented in vertical position.

Accordingly, in a first aspect of the invention, the present invention may be characterized broadly as providing a reactor system for a reaction catalyzed by ionic liquid, the reactor system comprising a first reaction zone and a first heat exchange zone. The first reaction zone comprises a reactor configured to receive ionic liquid and hydrocarbons and configured to provide a reactor effluent, the reactor comprising at least one static mixer disposed between an inlet and an outlet of the reactor. The first heat exchange zone comprises a heat exchanger having an inlet for cooling fluid, an outlet for cooling fluid, an inlet for process fluid, and, an outlet for a cooled process fluid, the outlet for the cooled process fluid being disposed below the inlet for the process fluid.

The reactor in the first heat exchange zone may comprise a plurality of static mixers. The static mixers from the plurality of static mixers may be spaced apart within the reactor between the inlet and outlet of the reactor.

The reactor in the first heat exchange zone may comprise a plurality of inlets for a hydrocarbon stream.

The heat exchanger in the heat exchange zone may comprise a vertically orientated heat exchanger. The heat exchanger in the first heat exchange zone may comprise a shell, a plurality of tubes inside of the shell, and a head separated from the shell by a tube sheet. The head of the heat exchanger may be configured to receive and discharge the cooling fluid. The head of the heat exchanger may comprise a through head inlet configured to receive the process fluid. A flow of the process fluid through the head of the heat exchanger may be generally parallel to a flow of the process fluid through the heat exchanger.

The reactor system may further comprise a second reaction zone having a second reactor and a second heat exchange zone having a second heat exchanger. The second reaction zone may be configured to receive a portion of the cooled process fluid from the first heat exchange zone, and the second heat exchanger may be configured to receive an effluent stream from the second reaction zone and provide the process fluid to the at least one vertical separation vessel in the separation zone.

In a second aspect of the invention, the present invention may be characterized broadly as providing a reactor system comprising a first reaction zone, a first heat exchange zone, and a separation zone. The first reaction zone comprises a vertical reactor having at least one static mixer disposed between a first end and a second end. The first heat exchange zone is in fluid communication with the first reaction zone and comprises a vertical heat exchanger having a vertical flow direction for a process fluid passing therethrough. The separation zone comprises at least one vertical separation vessel having an inlet, an outlet for ionic liquid, an outlet for a hydrocarbon effluent stream. The outlet for the hydrocarbon effluent stream may be disposed at a position above the outlet for ionic liquid.

The first reaction zone and the first heat exchange zone may comprise a stage, and the reactor system may further comprise a plurality of stages with each stage including a reaction zone and a heat exchange zone.

The reactor system may further comprise a pump configured to a provide a cooled process fluid stream from the first heat exchange zone and provide a recycle stream to the vertical reactor in the first reaction zone. The reactor system may further comprise a line configured to pass the cooled process fluid stream from the pump to a second reaction zone having a vertical reactor.

The vertical heat exchanger of the reactor system may comprise a head with an inlet for cooling fluid, an outlet for cooling fluid, an inlet for process fluid, and an outlet for cooled process fluid.

The vertical reactor of the reactor system may further comprise a plurality of inlets for a hydrocarbon stream and the inlets for a hydrocarbon stream each may be disposed upstream of a static mixer.

In a third aspect of the invention, the present invention may be characterized broadly as providing a process for alkylating hydrocarbons by: passing an olefin stream, an iC4 stream, and an ionic liquid catalyst stream through a first vertical reaction vessel in a generally vertical direction; dispersing the ionic liquid catalyst into droplets within the first vertical reaction vessel with at least one static mixer; operating the first vertical reaction vessel in order to alkylate the olefins from the olefin stream and provide a reactor effluent stream; injecting the reactor effluent stream into vertical heat exchanger in a generally vertical direction; removing heat from the reactor effluent stream in the vertical heat exchanger with a cooling fluid to provide a cooled effluent; and, separating at least a portion of the cooled effluent into an ionic liquid phase and a hydrocarbon phase in a vertical separation vessel.

The process may further comprise passing a portion of the cooled effluent to the first vertical reaction vessel as a recycle stream.

The process may further comprise injecting at least the olefin stream into the first vertical reaction vessel in a staged injection.

The reactor effluent stream may flow in a generally downward direction through the vertical heat exchanger.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

One or more new reactor systems have been invented which efficiently and effectively utilize ionic liquid catalyst. The plot space for accommodating the ionic liquid alkylation equipment is reduced by using reactors, heat exchangers, and/or separators that are oriented vertically. The savings in plot space is especially appreciable in reactor systems which have multiple stages. Additionally, not only do the various reactor systems reduce the plot space, but in view of the reactor systems, existing alkylation reactor systems that relied upon hydrofluoric acid or sulfuric acid as a catalyst can be revamped and repurposed to be used with ionic liquid alkylation technology. Thus, the present invention provides efficient and effective reactor systems for ionic liquid catalyzed reactions.

With these general principles in mind, one or more embodiments of the present invention will be described with the understanding that the following description is not intended to be limiting.

Figure 1:
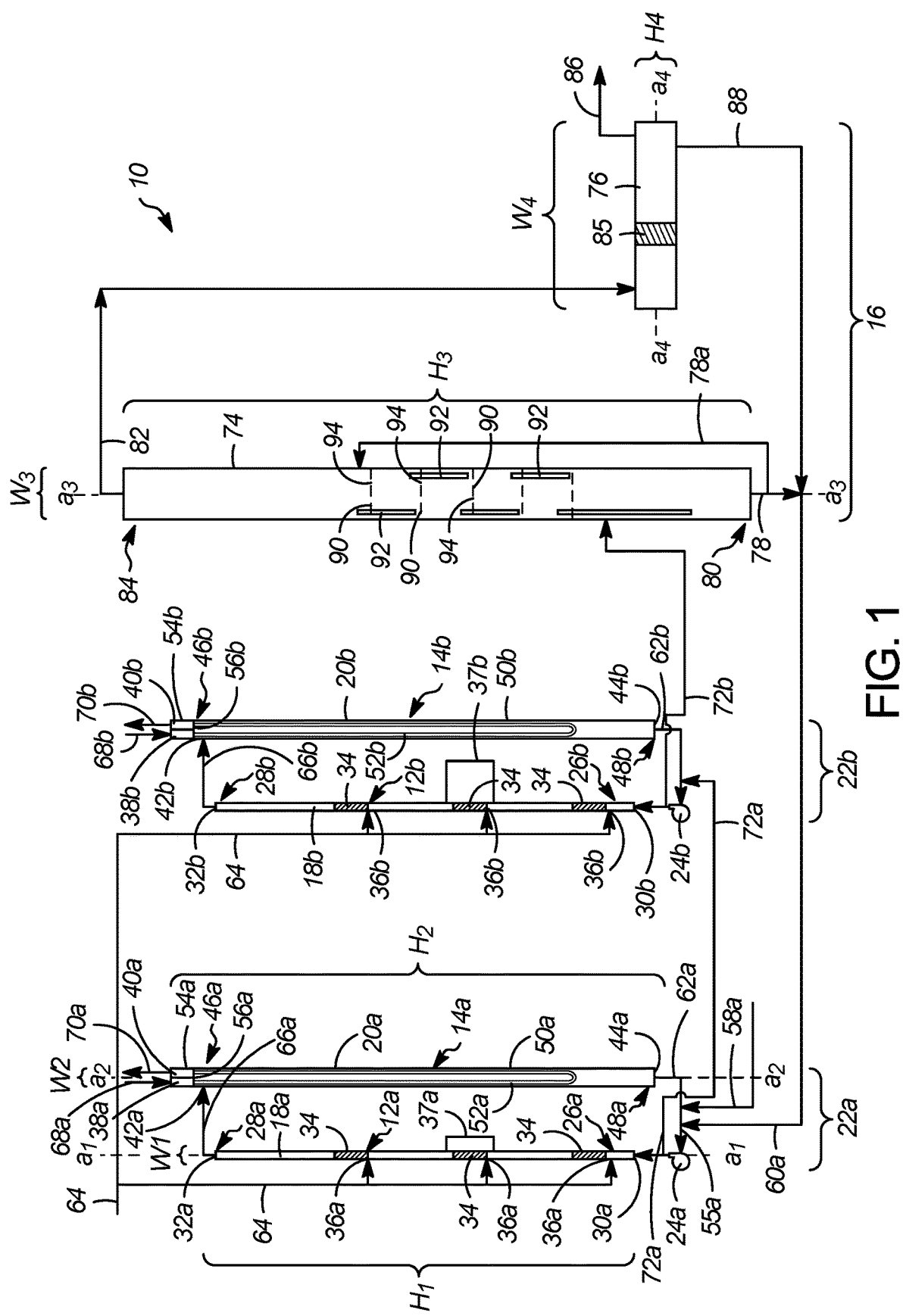
FIG. 1 shows a process flow diagram for a reactor system according to one or more embodiments of the present invention.

As shown in FIG. 1, a reactor system 10 according to an exemplary embodiment of the present invention comprises at least a first reaction zone 12a, a first heat exchange zone 14a, and a separation zone 16. The reaction zone 12a includes a reactor 18a and the heat exchange zone 14a includes a heat exchanger 20a. Together, the first reaction zone 12a and the first heat exchange zone 14a form a stage 22a of the reactor system 10. The reactor system 10 preferably comprises multiple stages 22a, 22b arranged in series, with each stage 22a, 22b preferably having a reaction zone 12a, 12b with a reactor 18a, 18b and a heat exchange zone 14a, 14b having a heat exchanger 20a, 20b. Having a reactor system 10 with multiple stages 22a, 22b arranged in series reduces the average alkylate concentration in the reaction zones 12a, 12b and minimizes further reaction of alkylate forming undesirable products. Pumps 24a, 24b may be used to circulate fluid between the reactors 18a, 18b and the heat exchangers 20a, 20b in each stage 22a, 22b, as well as transfer fluids to sequential stages 22a, 22b. Additionally, the transfer of fluids between stages 22a, 22b may also be accomplished by pressure difference between the stages 22a, 22b, for example by the second stage 22b being at a lower pressure than the first stage 22a. While the depicted reactor system 10 includes two stages 22a, 22b, each with a reaction zone 12a, 12b and a heat exchange zone 14a, 14b, any number of stages 22a, 22b may be used, and one or more of the stages 22a, 22b may include more than one reaction zone or one heat exchange zone.

With reference to the first reaction zone 12a, the reactor 18a preferably comprises a vertically orientated reactor, in which the height $H_1$ of the reactor 18a is much greater than its width $W_1$ and for which a longitudinal axis (along line $a_1$-$a_1$) of the reactor 18a is generally vertical. In one embodiment, the fluid within the reactor has an generally vertical flow direction that is upward meaning that overall in the reactor 18a, fluids flow from a bottom 26a of the reactor 18a to a top 28a of the reactor 18a. However, as will be discussed below in relation to FIG. 3, other configurations are contemplated.

The reactor 18a in the first reaction zone 12a is configured to receive ionic liquid and hydrocarbons and provide a reactor effluent. Accordingly, the reactor 18a includes an inlet 30a and an outlet 32a. As mentioned above, the fluid in the reactor 18a in FIG. 1 has a mostly vertical flow direction that is upward, and thus, the inlet 30a is disposed proximate the bottom 26a of the reactor 18a and the outlet 32a is disposed proximate the top 28a of the reactor 18a. Again, this is merely preferred.

The reactor 18a additionally includes at least one static mixer 34 disposed between the inlet 30a and the outlet 32a. In general, the static mixers 34 comprise mixing devices or structures that allow for the continuous blending of fluids within a pipe or vessel without any moving parts. In immiscible liquid systems, such as one with ionic liquid and hydrocarbons, the static mixers also disperse one of the phases, i.e., the ionic liquid, for increasing the contacting area between the two phases. As a result of the lack of moving parts, the static mixers 34 utilize the energy of the fluids flowing past to provide mixing and/or dispersion of the fluids. Exemplarily static mixers 34 include, bow tie, helical twist, grid type, corrugated plate or any other type of static mixer 34 that will disperse the ionic liquid and mix the droplets of ionic liquid and hydrocarbons. One exemplary static mixer 34 comprises an SMV™ mixer available from Sulzer Ltd., headquartered in Winterthur, Switzerland. See also U.S. Pat. No. 5,688,047 and GB Pat. No. 1 442 929. Preferably, the reactor 18*a* includes a plurality of static mixers 34 at various positions within the reactor 18*a* so that the ionic liquid is dispersed and mixed with the hydrocarbon reactants at multiple positions with limited pressure drops.

In order to control the reaction, the heat generated by the reaction, and to minimize the formation of undesired byproducts of the reaction, it is preferred that one of the hydrocarbons reactants is kept as a limiting reagent and the concentration of the second reactant is preferably well above the stoichiometric requirement. For example, with respect to an alkylation reaction with iC4 and olefinic hydrocarbons, it is preferred that the olefins are kept as the limiting reagent in order to minimize the side reactions of olefins with non-iC$_4$ hydrocarbons. Accordingly, in addition to the reactor 18*a* receiving one or more of the hydrocarbon reactants via the inlet 30*a*, the reactor 18*a* may also have one or more additional inlets 36*a*, or injection points, for a hydrocarbon stream disposed along the height H1 of the reactor 18*a*, preferably being spaced out between the inlet 30*a* and the outlet 32*a* of the reactor 18*a*. The additional inlets 36*a* can be spaced apart equally, if desired. Additionally, the amount of hydrocarbon injected at additional inlet 36*a* can be the same or different, as desired.

Preferably, the additional inlets 36*a* are used so that the reactor 18*a* includes a staged injection, in which the limiting reagent is injected at various points between the inlet 30*a* and the outlet 32*a* of the reactor 18*a*. It is preferred that the additional inlets 36*a* are disposed proximate and upstream of a static mixer 34 so that upon injection into the reactor the reagents will pass into the static mixers 34.

Turning to the heat exchanger 20*a* in the heat exchange zone 14*a*, the heat exchanger 20*a* includes an inlet 38*a* for cooling fluid and an outlet 40*a* for cooling fluid, as well as an inlet 42*a* for process fluid and an outlet 44*a* for process fluid. As decided in FIG. 1, the heat exchanger 20*a* preferably comprises a vertically orientated heat exchanger, in which the height H$_2$ of the heat exchanger 20*a* is much greater than its width W$_2$ and a longitudinal axis (along line a$_2$-a$_2$) of the heat exchanger 20*a* is generally vertical.

The process fluid flowing within the heat exchanger 20*a*, may have a mostly or primarily vertical flow direction that may be downward meaning that, overall, the process fluids flow from a top 46*a* of the heat exchanger 20*a* towards a bottom 48*a* of the heat exchanger 20*a*. It is advantageous for process fluid to flow down in the heat exchangers to reduce the coalescing and accumulation of the heavy, viscous ionic liquid and its impact on heat transfer. However, as discussed below with respect to FIG. 3 this is merely preferred.

In general, the heat exchanger 20*a* may be any design, for example, a tube in shell heat exchanger, a spiral plate heat exchanger, or a hairpin heat exchanger to name a few exemplary heat exchangers. As depicted in FIG. 1, the heat exchanger 20*a* may comprises a shell 50*a*, a plurality of tubes 52*a* inside the shell 50*a* and a head 54*a* separated from the shell 50*a* by a tube sheet 56*a*. The tubes 52*a* may be U-shaped, twisted tubes, and/or fin tubes. The head 54*a* of the heat exchanger 20*a* may be configured to receive the cooling fluid and discharge the cooling fluid. The shell 50*a* of the heat exchanger 20*a* may be configured to receive process fluid, i.e., the effluent from the reactor 18*a*, and discharge the process fluid, i.e. cooled effluent from the reactor 18*a*. It is also contemplated but not depicted that the process fluid is received and discharged by the head 54*a* of the heat exchanger 20*a*, and that the cooling fluid is received and discharged by the shell 50*a* of the heat exchanger 20*a*.

Figure 2:
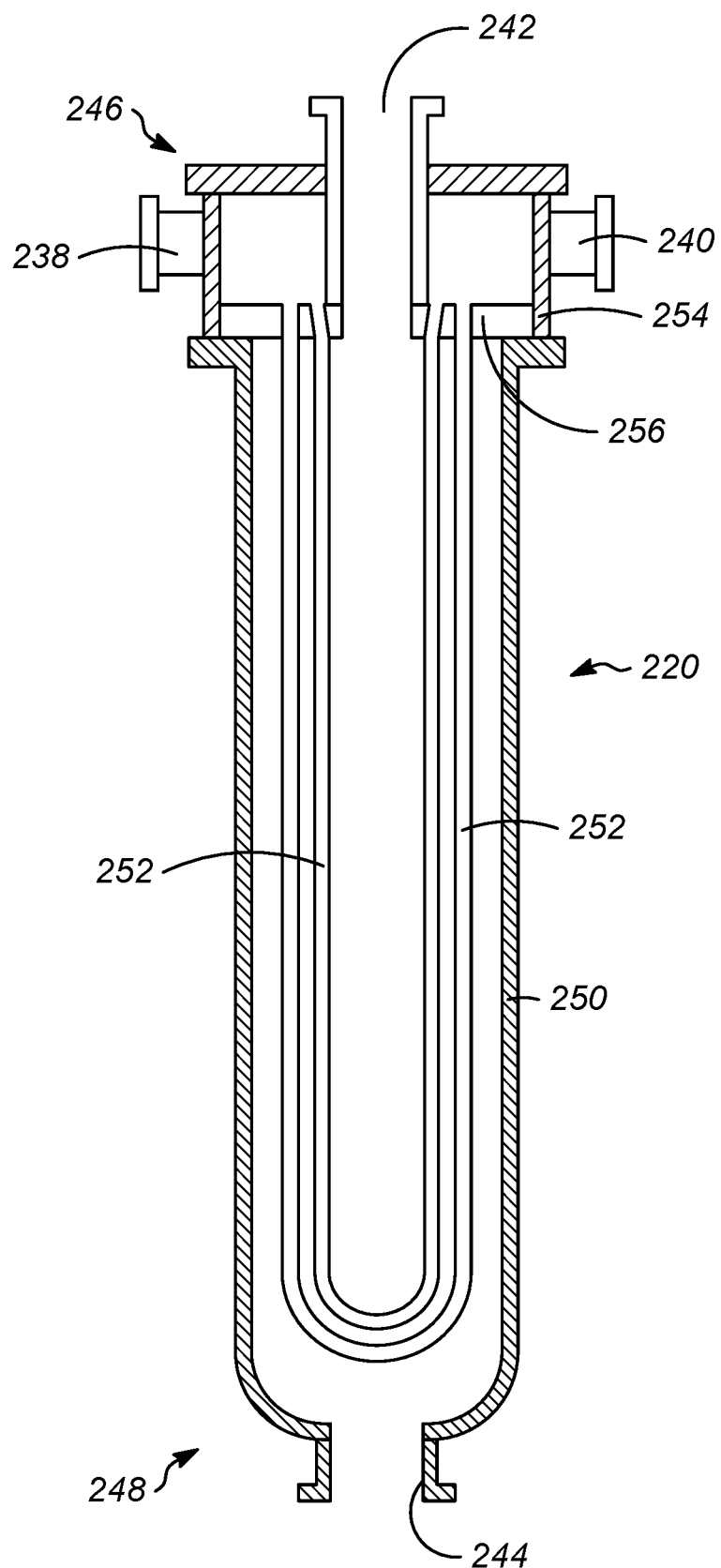
FIG. 2 shows a side cutaway view of a heat exchanger used according to one or more embodiments of the present invention; and, FIG. 3 shows another process flow diagram for a reactor system according to one or more embodiments of the present invention.

Turning to FIG. 2, an alternative configuration for a heat exchanger is shown in elements in FIG. 2 which are similar to elements in FIG. 1 are depicted with similar reference numerals with the reference numerals in FIG. 2 being increased by a factor of "200."

The heat exchanger 220 in FIG. 2, comprises a first end 246, a second end 248, a shell 250, a plurality of u-shaped tubes 252 inside the shell 250, and a head 254 separated from the shell 250 by a tube sheet 256. In addition to the head 254 being configured to receive and discharge the cooling fluid, via an inlet 238 and an outlet 240, respectively, the head 254 is also configured to receive the process fluid. Accordingly, as shown in FIG. 2, the head 254 of the heat exchanger 220 includes an inlet 242 for the process fluid, while the shell 250 of the heat exchanger 220 includes the outlet 244 for the process fluid. Once the process fluid is injected into the inlet 242, it may pass through the tube sheet 256, flow into the shell 250 of the heat exchanger 220 where the cooling fluid in the tubes 252 may remove heat. The cooled process fluid may be passed out of the heat exchanger 220 via the outlet 244.

As will be appreciated, with the injection of the process fluid through the head 254, the process fluid can be injected into the heat exchanger 220 parallel to the overall flow of the process fluid through the heat exchanger 220. This is believed to provide a better flow for the process fluid compared to heat exchangers in which the process fluid is injected in a direction that is different than the direction of the process fluid flowing through the heat exchanger. More specifically, it is thought that such will better maintain the ionic liquid in a dispersion and minimizing the coalescing of same. Again, this will minimize the coalescing of ionic liquid droplets and the separation of the ionic liquid from the hydrocarbons. Additionally, it is contemplated that within the heat exchanger 220 (or within any heat exchange zones) the reaction may further proceed provided that reactants and ionic liquid catalyst are present in the fluids passing through the heat exchanger 220. Thus, it is to be understood that in the practicing of the present invention, reactions may occur within a heat exchange zone and/or a heat exchanger.

Returning to FIG. 1, the use of this embodiment of the reactor system 10 of the present application for an alkylation reaction using ionic liquid as a catalyst will be described. However, this is only intended as exemplary and one of ordinary skill in the art will appreciate that the reactor system may be utilized with different reactions being catalyzed by ionic liquid.

In use, a mixed stream 55*a* comprising a mixture of a hydrocarbon stream 58*a* and an ionic liquid stream 60*a* may be mixed and passed or injected into the reactor 18*a* of the first reaction zone 12*a* through the inlet 30*a* of the reactor 18*a* by the pump 24*a*. The hydrocarbon stream 58*a* may comprise recycle iC4 hydrocarbons. The mixed stream 55*a* preferably also comprises a cooled effluent 62*a*, as will be discussed below. Alternatively, the ionic liquid stream 60*a* and the hydrocarbon stream 58*a* may be each separately injected or passed into the reactor 18*a*.

Within the reactor, the ionic liquid may be dispersed into fine droplets in the static mixers 34. Additionally, the reactants, iC4 mainly from stream 55*a* and olefins mainly from inlets 36*a*, may be mixed by the static mixers 34. The ionic liquid acid catalyst promotes an alkylation reaction between the reactants. In order to control the reaction, reaction temperature and minimize the production of undesired by products, the olefins may comprise a limiting reagent for the alkylation reaction. A local iC4 to olefin ratio may be increased by injecting an olefin stream 64 via a staged injections, i.e., at the additional inlets 36a along the height $H_1$ of the reactor 18a. In one example, a local iC4 to olefins ratio ("I/O") of about 180 may be utilized and produced by utilizing an overall feed I/O of about 10 (including recycle iC4), a circulation volumetric rate about 3 times the feed rate between the reaction zone 12a and the heat exchange zone 14a, and utilizing two stages 22a, 22b, each having a reactor 18a, 18b with three additional inlets 36a, 36b for olefins/iC4 injection. The local I/O can be adjusted by varying the pump-around rate, the number of stages 22a, 22b in series, or the number of additional inlets 36a, 36b for olefins/iC4 injection. The temperature rise in the reactors 18a, 18b may be less than about 15° F. and preferably less than 10° F. due to the heat of reaction removed in the heat exchangers 20a, 20b. Additionally, bypass lines 37a may be provided to allow for flow of the process fluids around one or more static mixers to further control the rate of reaction and temperature rise.

The injected fluid and the pump-around fluid already in the reactor 18a containing ionic liquid acid catalyst and iC4 flow upward together through the static mixers 34 for ionic liquid dispersion, fluid mixing and reaction and the reactor 18a provides a reaction effluent 66a. The reaction effluent 66a may then be passed to the heat exchanger 20a for heat removal and, possibly, for further reaction of any olefins that may still remain in the reaction effluent 66a.

A cooling fluid stream 68a may be passed into the heat exchanger 20a in the heat exchange zone 14b and can remove heat from the reaction effluent 66a via heat exchange. A heated cooling fluid 70a may be withdrawn from the heat exchanger 20a and may be passed to a cooling system (not shown), or may be used to heat another process stream. After the heated cooling fluid 70a is cooled, it may returned to the heat exchanger 20a to again remove heat from the reaction effluent 66a. The cooled effluent stream 62a may be recovered proximate the bottom 48a of the heat exchanger 20a. The cooled effluent stream 62a, may be passed back to the reactor 18a as mentioned above. Additionally, a portion 72a of the mixed stream 55a may be passed to the second stage 22b via the pump 24a as shown in FIG. 1 where stream 72a is sent to the inlet of pump 24b. Alternatively, the stream 72a can also be sent to the outlet of the pump 24b via pressure difference between stages 22a and 22b.

The second stage depicted in FIG. 1 may be operated in the same or similar manner, in which elements similar to the first stage 22a are depicted with the indicator "b" instead of "a." The portion 72a of the cooled effluent stream 62a includes iC4 hydrocarbons, as well as ionic liquid. It may be mixed with the cooled effluent stream 62b from the heat exchanger 20b in the second heat exchange zone 14b. The olefin stream 64 may be injected into the reactor 18b in the second reaction zone 12b, via the additional inlets 36b. Again, the static mixers 34 will mix the reactants and disperse the ionic liquid to produce an effluent 66b which may be cooled in the heat exchanger 20b in the second heat exchange zone 14b. From the heat exchanger 20b in the second heat exchange zone 14b, the cooled effluent 62b may be passed back to the reactor 18b in the second reaction zone 12b with a portion 72b being passed from the second stage 22b to the separation zone 16.

In the separation zone 16, a net effluent from the reaction zone(s) 12a, 12b is separated into ionic liquid and hydrocarbons.

In an exemplary separation zone 16, the separation zone 16 includes a primary separation vessel 74 and a secondary separator vessel 76. In the primary separation vessel 74, the effluent may be separated into an ionic liquid phase and a hydrocarbon phase by gravity. The primary separation vessel 74 preferably comprises a vertically orientated separation vessel, in which the height $H_3$ of the primary separation vessel 74 is much greater than its width $W_3$ and a longitudinal axis (along line $a_3$-$a_3$) of the primary separation vessel 74 is generally vertical. An ionic liquid stream 78 may be withdrawn proximate a bottom 80 of the primary separation vessel 74, and may be used as the stream 60a of ionic liquid passed into the reactor 18a in the first reaction zone 12a. A hydrocarbon phase stream 82 may be withdrawn proximate a top 84 of the primary separation vessel 74. The hydrocarbon phase stream 82 may be passed to the secondary separator vessel 76 and/or other treating devices for removing residual ionic liquid in the hydrocarbon phase stream 82.

For example, the secondary separator vessel 76 in the separation zone 16 may comprise a horizontally orientated separation vessel in which the height $H_4$ of the secondary separation vessel 76 is much less than its width $W_4$ and a longitudinal axis (along line $a_4$-$a_4$) of the secondary separation vessel 76 is generally horizontal. The secondary separation vessel 76 may also include coalescing element 85 which may comprise coalescing medium or the like to enlarge any entrained fine droplets of ionic liquid and then to remove them from the hydrocarbons. A hydrocarbon effluent stream 86 may be withdrawn from the secondary separator vessel 76 and passed to a product recovery zone (not shown) which may include one or more distillation columns for separating a stream of alkylate product from the hydrocarbon effluent stream 86. Any unreacted iC4 may be received in the product recovery zone, for example, by being withdrawn from an upper part of a distillation column, and recycled back to the reaction zone as the hydrocarbon stream 58a. Any ionic liquid recovered from the secondary separation vessel 76 may be combined, via a line 88, with the ionic liquid stream 78 from the primary separation vessel 74.

Although not depicted as such, the hydrocarbon phase stream 82 from the primary separation vessel 74 may be passed to the product recovery zone (and thus a secondary separation vessel 76 may not be included in the separation zone 16).

The primary separation vessel 74 may include one or more trays 90 for improving the separation of ionic liquid from hydrocarbons. A stream 78a of the ionic liquid stream 78 from the primary separation vessel 74 may be passed back into the top tray in primary separation vessel 74. Within primary separation vessel 74, the recycle ionic liquid 78a may flows across each of the trays 90 and down through a downcomer 92 from tray 90 to tray 90. The hydrocarbons containing ionic liquid droplets rise through perforations 94 in the trays 90 trays forming thin jets or droplets in the continuous ionic liquid phase formed on the tray 90. Through the contacting between the dispersed hydrocarbon phase and the continuous ionic liquid phase, the ionic droplets in the hydrocarbon phase are collected by the ionic liquid phase so that the concentration of the ionic liquid in the hydrocarbon is reduced after passing through each tray 90. A detailed description of such a separation vessel is described in U.S. Pat. Pub. No. 2015/0274614, the entirety of which is incorporated herein by referenced.

Figure 3:
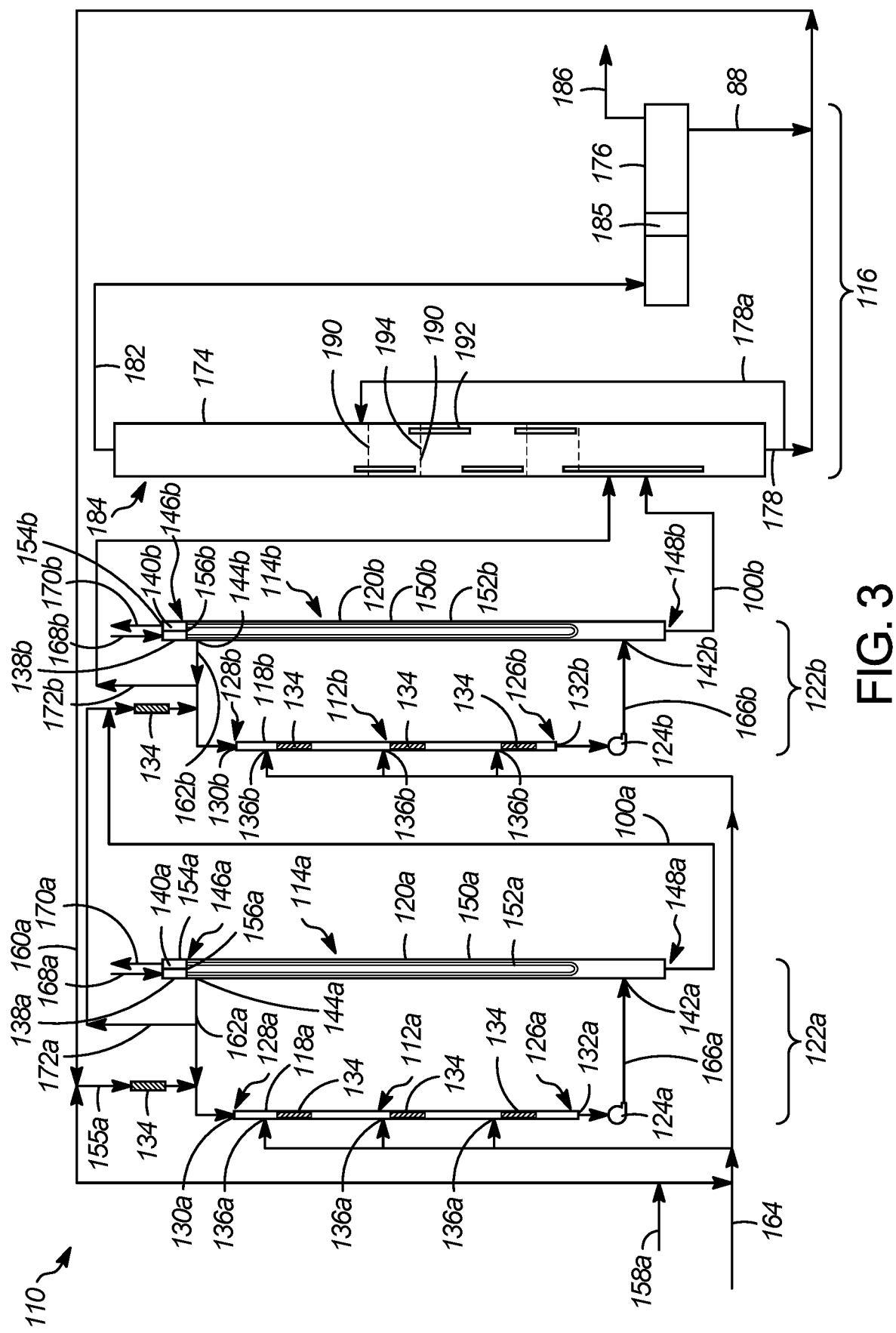

In FIG. 3, another reactor system 110 is shown in which the flow of the process fluid through the reactors 118a, 118b is in a downward direction, while the flow through the heat exchangers 120a, 120b is in an upward direction. The reactor system 110 of FIG. 3 will be described in relation to an alkylation reaction using ionic liquid, however this is only intended as exemplary and one of ordinary skill in the art will appreciate that the reactor system 110 may be utilized with different reactions. Elements in FIG. 3 which are similar to elements in FIG. 1 are depicted with similar reference numerals with the reference numerals in FIG. 3 being increased by a factor of "100."

A mixed stream 155a comprising a mixture of a hydrocarbon stream 158a and an ionic liquid stream 160a may be passed through a static mixer 134, combined a portion of a cooled effluent stream 162a, and then passed to a reactor 118a in a reaction zone 112a. The streams 155a and 162a may be injected into the reactor via the inlet 130a, which is disposed proximate the top 128a of the reactor 118a. An olefin stream 164 is also provided to the first reaction zone 112a. The olefin stream 164 may be mixed with a portion of the hydrocarbon stream 158a and then injected into the reactor 118a. Again, preferably the olefin stream 164 is injected or passed into the reactor 118a via a staged injection to increase the local iC4/olefin ratio and avoid undesired byproducts as well as to control temperature distribution in the reactor. Static mixers 134 in the reactor 118a will disperse ionic liquid and mix the reactants and the dispersed ionic liquid catalyst promoting the alkylation reaction.

From the reactor 118a in the first reaction zone 112a, the reaction effluent 166a may be passed to the heat exchanger 120a in the first heat exchange zone 114a. In the heat exchanger 120a, the cooling fluid stream 168a will absorb heat from the reactants, and the process fluid at the outlet 144a of the heat exchanger 120a will have a lower temperature than the process fluid at the inlet 142a of the heat exchanger 120a. The cooled effluent stream 162a may be passed back to the reactor 118a in the first reaction zone 112a. A portion 172a of the cooled effluent stream 162a may be passed to the second stage 122b of the reactor system 110.

The second stage 122b of the reactor system 110 is similar to the first stage 122a. A portion 172b of the cooled effluent 162b from the heat exchanger 120b may be passed to the separation zone 116 of the reactor system 110. The separation zone 116 is preferably the same as that in FIG. 1 and thus, that portion of the above description is herein incorporated by reference.

Since the flow of fluids in the heat exchanger(s) 120a, 120b in FIG. 3 is upward, a line 100a, 100b may be provided for each stage 122a, 122b to remove ionic liquid that has settled to the bottom 148a, 148b of the heat exchangers 120a, 120b. Depending on the positioning of the stage 122a, 122b, a line 100a may pass ionic liquid from the heat exchanger 120a to the hydrocarbon stream 172a before entering into the second (or next) stage 122b, or a line 100b may pass ionic liquid from the heat exchanger 120b to the separation zone 116. Other configurations are contemplated.

In either depicted configuration, by utilizing vertically orientated reactors and heat exchangers, the reactor systems of the present invention allow for a reduction in the plot space and for revamp of existing alkylation unit with sulfuric acid or HF acid catalyst.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Specific Embodiments

While the following is described in conjunction with specific embodiments, it will be understood that this description is intended to illustrate and not limit the scope of the preceding description and the appended claims.

A first embodiment of the invention is a reactor system for a reaction catalyzed by ionic liquid, the reactor system comprising a first reaction zone having a reactor configured to receive ionic liquid and hydrocarbons and configured to provide a reactor effluent, the reactor comprising at least one static mixer disposed between an inlet and an outlet of the reactor; and, a first heat exchange zone comprising a heat exchanger having an inlet for cooling fluid, an outlet for cooling fluid, an inlet for process fluid, and, an outlet for a cooled process fluid, the outlet for the cooled process fluid being disposed below the inlet for the process fluid. An embodiment of the invention is one, any or all of prior embodiments in this paragraph up through the first embodiment in this paragraph wherein the reactor comprises a plurality of static mixers. An embodiment of the invention is one, any or all of prior embodiments in this paragraph up through the first embodiment in this paragraph wherein the static mixers from the plurality of static mixers are spaced apart within the reactor between the inlet and outlet of the reactor. An embodiment of the invention is one, any or all of prior embodiments in this paragraph up through the first embodiment in this paragraph wherein the reactor comprises a plurality of inlets for a hydrocarbon stream. An embodiment of the invention is one, any or all of prior embodiments in this paragraph up through the first embodiment in this paragraph wherein the heat exchanger in the heat exchange zone comprises a vertically orientated heat exchanger. An embodiment of the invention is one, any or all of prior embodiments in this paragraph up through the first embodiment in this paragraph wherein the heat exchanger in the first heat exchange zone comprises a shell, a plurality of tubes inside of the shell, and a head separated from the shell by a tube sheet. An embodiment of the invention is one, any or all of prior embodiments in this paragraph up through the first embodiment in this paragraph wherein the head of the heat exchanger is configured to receive and discharge the cooling fluid. An embodiment of the invention is one, any or all of prior embodiments in this paragraph up through the first embodiment in this paragraph wherein the head of the heat exchanger comprises a through head inlet configured to receive the process fluid. An embodiment of the invention is one, any or all of prior embodiments in this paragraph up through the first embodiment in this paragraph wherein a flow of the process fluid through the head is generally parallel to a flow of the process fluid through the heat exchanger. An embodiment of the invention is one, any or all of prior embodiments in this paragraph up through the first embodiment in this paragraph further comprising a second reaction zone having a second reactor; and, a second heat exchange zone having a second heat exchanger, the second reaction zone configured to receive a portion of the cooled process fluid from the first heat exchange zone, and the second heat exchanger configured to receive an effluent stream from the second reaction zone and provide the process fluid to the at least one vertical separation vessel in the separation zone.

A second embodiment of the invention is a reactor system comprising a first reaction zone comprising a vertical reactor having at least one static mixer disposed between a first end and a second end; a first heat exchange zone in fluid communication with the first reaction zone and comprising a vertical heat exchanger having a vertical flow direction for a process fluid passing therethrough; and, a separation zone comprising at least one vertical separation vessel having an inlet, an outlet for ionic liquid, an outlet for a hydrocarbon effluent stream, the outlet for the hydrocarbon effluent stream disposed at a position above the outlet for ionic liquid. An embodiment of the invention is one, any or all of prior embodiments in this paragraph up through the second embodiment in this paragraph, wherein the first reaction zone and the first heat exchange zone comprise a stage, and wherein the reactor system comprises a plurality of stages with each stage includes a reaction zone and a heat exchange zone. An embodiment of the invention is one, any or all of prior embodiments in this paragraph up through the second embodiment in this paragraph further comprising a pump configured to a provide a cooled process fluid stream from the first heat exchange zone and provide a recycle stream to the vertical reactor in the first reaction zone. An embodiment of the invention is one, any or all of prior embodiments in this paragraph up through the second embodiment in this paragraph further comprising a line configured to pass the cooled process fluid stream from the pump to a second reaction zone having a vertical reactor. An embodiment of the invention is one, any or all of prior embodiments in this paragraph up through the second embodiment in this paragraph wherein the vertical heat exchanger comprises a head with an inlet for cooling fluid, an outlet for cooling fluid and an inlet for process fluid and an outlet for cooled process fluid. An embodiment of the invention is one, any or all of prior embodiments in this paragraph up through the second embodiment in this paragraph wherein the vertical reactor further comprises a plurality of inlets for a hydrocarbon stream, wherein the inlets for a hydrocarbon stream are each disposed upstream of a static mixer.

A third embodiment of the invention is a process for alkylating hydrocarbons, the process comprising passing an olefin stream, an iC4 stream, and an ionic liquid catalyst stream through a first vertical reaction vessel in a generally vertical direction; dispersing the ionic liquid catalyst into droplets within the first vertical reaction vessel with at least one static mixer; operating the first vertical reaction vessel in order to alkylate the olefins from the olefin stream and provide a reactor effluent stream; injecting the reactor effluent stream into vertical heat exchanger in a generally vertical direction; removing heat from the reactor effluent stream in the vertical heat exchanger with a cooling fluid to provide a cooled effluent; and, separating at least a portion of the cooled effluent into an ionic liquid phase and a hydrocarbon phase in a vertical separation vessel. An embodiment of the invention is one, any or all of prior embodiments in this paragraph up through the third embodiment in this paragraph further comprising passing a portion of the cooled effluent to the first vertical reaction vessel as a recycle stream. An embodiment of the invention is one, any or all of prior embodiments in this paragraph up through the third embodiment in this paragraph further comprising injecting at least the olefin stream into the first vertical reaction vessel in a staged injection. An embodiment of the invention is one, any or all of prior embodiments in this paragraph up through the third embodiment in this paragraph, wherein the reactor effluent stream flows in a generally downward direction through the vertical heat exchanger.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A reactor system for a reaction catalyzed by ionic liquid, the reactor system comprising:
   a first reaction zone comprising a vertically orientated reactor having a height greater than a width, the vertically orientated reactor a configured to receive ionic liquid and hydrocarbons and further configured to provide a reactor effluent, the reactor comprising at least one static mixer disposed within the vertically orientated reactor between an inlet and an outlet of the vertically orientated reactor, and the inlet being disposed lower along the height of the vertically orientated reactor than the outlet; and,
   a first heat exchange zone comprising a heat exchanger comprising an inlet for cooling fluid, an outlet for cooling fluid, an inlet for the reactor effluent, and, an outlet for a cooled reactor effluent, wherein the outlet for the cooled process fluid is disposed below the inlet for the process fluid.

2. The reactor system of claim 1 wherein the vertically orientated reactor comprises a plurality of static mixers.

3. The reactor system of claim 2 wherein the static mixers from the plurality of static mixers are spaced apart within the vertically orientated reactor between the inlet and outlet of the vertically orientated reactor.

4. The reactor system of claim 1 wherein the vertically orientated reactor comprises a plurality of inlets for a hydrocarbon stream.

5. The reactor system of claim 1 wherein the heat exchanger in the first heat exchange zone comprises a vertically orientated heat exchanger.

6. The reactor system of claim 1 wherein the heat exchanger in the first heat exchange zone comprises a shell, a plurality of tubes inside of the shell, and a head separated from the shell by a tube sheet.

7. The reactor system of claim 6 wherein the head of the heat exchanger is configured to receive and to discharge the cooling fluid.

8. The reactor system of claim 6 wherein the head of the heat exchanger comprises a through head inlet configured to receive the process fluid.

9. The reactor system of claim 6 wherein a flow of the process fluid through the head is generally parallel to a flow of the process fluid through the heat exchanger.

10. The reactor system of claim 1 further comprising:
    a second reaction zone comprising a second vertically orientated reactor; and,
    a second heat exchange zone comprising a second heat exchanger, the second reaction zone configured to receive a portion of the cooled reactor effluent from the first heat exchange zone, and the second heat exchanger configured to receive an effluent stream from the second reaction zone and configured to provide a cooled effluent stream to a separation vessel.

11. A reactor system comprising:
a first reaction zone comprising a vertical reactor having at least one static mixer disposed between a first end and a second end;
a first heat exchange zone in fluid communication with the first reaction zone and comprising a vertical heat exchanger having a vertical flow direction for a process fluid flowing therethrough; and,
a separation zone comprising at least one vertical separation vessel having an inlet, an outlet for ionic liquid, and an outlet for a hydrocarbon effluent stream, the outlet for the hydrocarbon effluent stream disposed position above the outlet for ionic liquid.

12. The reactor system of claim 11, wherein the first reaction zone and the first heat exchange zone each comprise a stage, and wherein the reactor system further comprises a plurality of stages with each stage includes a reaction zone and a heat exchange zone.

13. The reactor system of claim 11 further comprising:
a pump configured to provide a cooled process fluid stream from the first heat exchange zone and configured to provide a recycle stream to the vertical reactor in the first reaction zone.

14. The reactor system of claim 13 further comprising a line configured to pass the cooled process fluid stream from the pump to a second reaction zone comprising a vertical reactor.

15. The reactor system of claim 11 wherein the vertical heat exchanger comprises a head with an inlet for cooling fluid, an outlet for cooling fluid, an inlet for process fluid, and an outlet for cooled process fluid.

16. The reactor system of claim 11 wherein the vertical reactor further comprises a plurality of inlets for a hydrocarbon stream, and wherein the inlets for a hydrocarbon stream are each disposed upstream of a static mixer.

17. A process for alkylating hydrocarbons, the process comprising:
passing an olefin stream, an iC4 stream, and an ionic liquid catalyst stream into a first vertical reaction vessel, wherein the first vertical reaction vessel has a generally vertical flow direction for fluid therein;
dispersing the ionic liquid catalyst into droplets within the first vertical reaction vessel with at least one static mixer;
operating the first vertical reaction vessel in order to alkylate olefins from the olefin stream and provide a reactor effluent stream;
injecting the reactor effluent stream into vertical heat exchanger in a generally vertical direction;
removing heat from the reactor effluent stream in the vertical heat exchanger with a cooling fluid to provide a cooled effluent; and,
separating at least a portion of the cooled effluent into an 10 mc liquid phase and a hydrocarbon phase in a vertical separation vessel.

18. The process of claim 17 further comprising:
passing a portion of the cooled effluent to the first vertical reaction vessel as a recycle stream.

19. The process of claim 17 further comprising:
passing at least the olefin stream into the first vertical reaction vessel in a staged injection.

20. The process of claim 17, wherein the reactor effluent stream flows in a generally downward direction through the vertical heat exchanger.

* * * * *